(12) United States Patent
Jenkins et al.

(10) Patent No.: US 7,485,466 B2
(45) Date of Patent: Feb. 3, 2009

(54) PROTEIN DETECTION SYSTEM

(75) Inventors: Dennis B. Jenkins, Pleasanton, CA (US); Edward B. Tucker, Willowbrook, IL (US); Timothy E. Kozikoski, Willowbrook, IL (US)

(73) Assignee: The Clorox Company, Oakland, CA (US)

( * ) Notice: Subject to any disclaimer, the term of this patent is extended or adjusted under 35 U.S.C. 154(b) by 640 days.

(21) Appl. No.: 11/140,795

(22) Filed: May 31, 2005

(65) Prior Publication Data

US 2006/0270051 A1 Nov. 30, 2006

(51) Int. Cl.
*G01N 33/00* (2006.01)
*A01K 29/00* (2006.01)

(52) U.S. Cl. .......................... 436/86; 119/173
(58) Field of Classification Search ................. 119/170, 119/171, 172, 173; 436/86
See application file for complete search history.

(56) References Cited

U.S. PATENT DOCUMENTS

| 2,986,453 A | 5/1961 | Collins |
|---|---|---|
| 3,063,812 A | 11/1962 | Collins |
| 3,485,587 A | 12/1969 | Keston |
| 4,402,941 A | 9/1983 | Vaillancourt |
| 4,641,605 A | 2/1987 | Gordon |
| 5,005,520 A | 4/1991 | Michael |
| 5,143,023 A | 9/1992 | Kuhns |
| 5,267,532 A | 12/1993 | Franklin et al. |
| 5,328,850 A | 7/1994 | Corey |
| 5,359,960 A | 11/1994 | Yananton |
| 5,371,054 A | 12/1994 | Pluta et al. |
| 5,403,744 A | 4/1995 | Zimmerle |
| 5,655,480 A | 8/1997 | Steckel |
| 5,685,259 A | 11/1997 | Santioemmo et al. |
| 5,775,259 A * | 7/1998 | Tucker ........................ 119/173 |
| 5,780,385 A | 7/1998 | Santioemmo et al. |
| 5,830,765 A | 11/1998 | Santioemmo et al. |
| 6,019,062 A | 2/2000 | Lombard et al. |

FOREIGN PATENT DOCUMENTS

| WO | WO 96/17245 | 6/1996 |
|---|---|---|
| WO | WO 98/58533 | 12/1998 |
| WO | WO 2004015423 | * 2/2004 |

* cited by examiner

*Primary Examiner*—Jill Warden
*Assistant Examiner*—Timothy G Kingan
(74) *Attorney, Agent, or Firm*—Ann Lee

(57) ABSTRACT

A system for detecting protein in mammalian urine is disclosed herein. Phloxine B buffered between pH 2-2.5 undergoes a color change from colorless to red in the presence of protein. Disclosed herein are animal litter compositions and additives comprising Phloxine B and a protein-sequestering agent buffered at a pH below about 3 which detect the presence of protein at levels indicative of ill-health in feline urine.

18 Claims, 3 Drawing Sheets no pH change
Protein

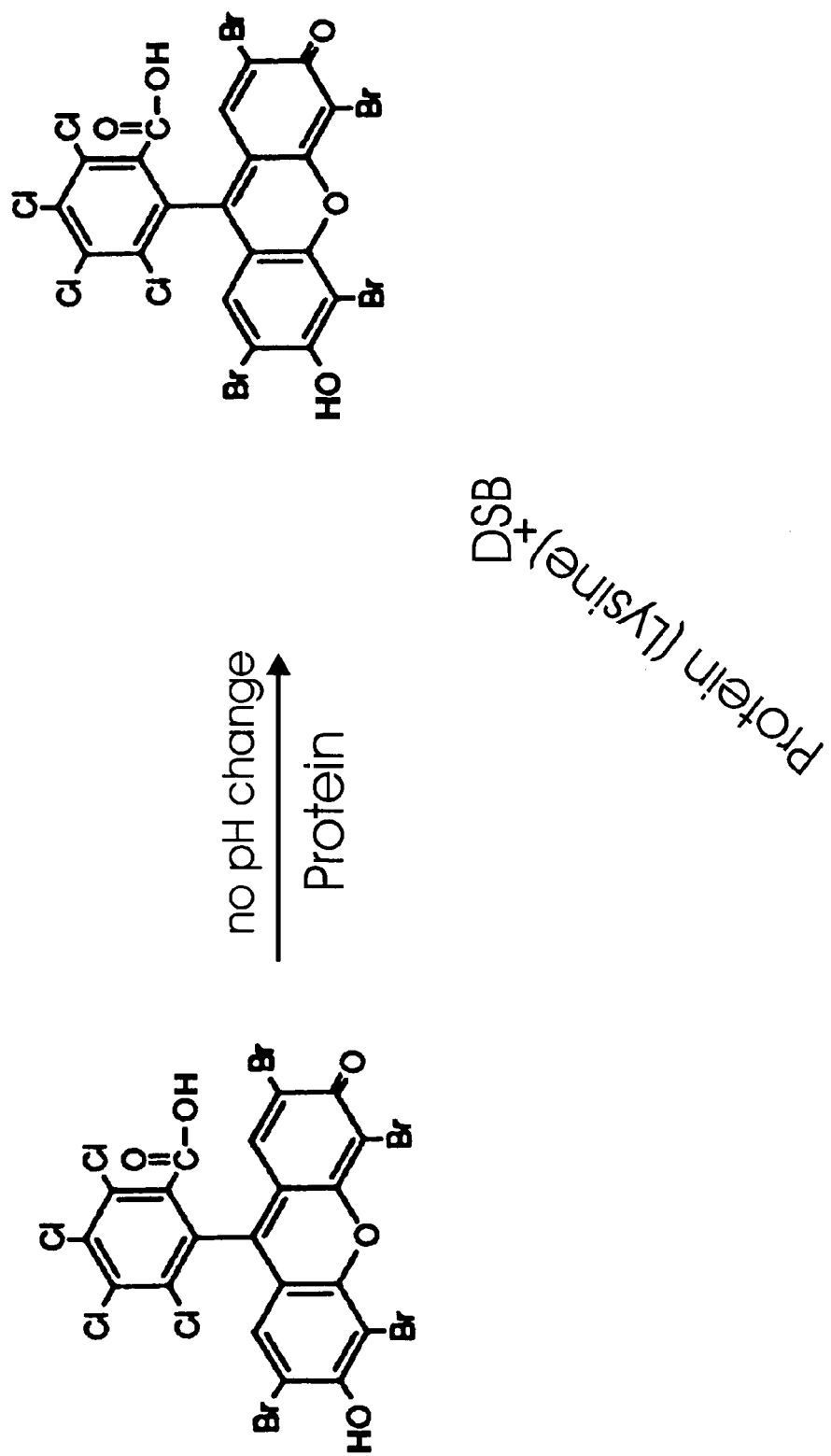

PROTEIN DETECTION SYSTEM

FIELD OF THE INVENTION

The present invention relates generally to protein detection. In particular detection of protein in feline urine is discussed.

BACKGROUND OF THE INVENTION

The presence of protein in certain bodily fluids can be an indication of illness. For example, the presence of elevated protein levels in feline urine can indicate kidney disease, a significant cause of cat illness and death.

SUMMARY OF THE INVENTION

An aspect of the invention includes an animal litter additive comprising: MB Macroporous silica gel buffered at a pH below about 3 containing a mixture of a protein-sequestering agent and Phloxine, wherein said protein-sequestering agent is present in an amount effective at blocking the attachment of Phloxine to protein at a predetermined protein level.

Another aspect of the invention includes a protein detection method comprising: providing a sample; contacting said sample with Phloxine; and detecting the presence of protein in said sample, wherein a color change is observed if said sample contains said protein.

A further aspect of the invention includes an animal litter comprising: an absorbent material suitable for use as an animal litter, wherein at least a portion of said litter contains Phloxine, wherein said Phloxine-containing portion of litter is below about pH3.

BRIEF DESCRIPTION OF THE DRAWINGS

Further features and advantages will become apparent from the following accompanying drawings.

FIG. 3 illustrates a mechanism by which a protein sequestering agent inhibits the attachment of Phloxine to protein.

DETAILED DESCRIPTION OF THE INVENTION

Protein levels in mammalian bodily fluids can be indicators of disease. The ability to detect these proteins in samples of various mammalian urine is disclosed herein. Bovine serum albumin is used as a representative protein to evaluate the various detection embodiments disclosed herein. The methods of the present invention are effective for detecting protein in urine samples from mammals, e.g., humans, felines, canines, and rodents. The animal litter disclosed herein could be used for common pets, cats, dogs, gerbils, guinea pigs, mice and hamsters, rabbits, ferrets and laboratory animals (e.g., mice, rats, and the like).

Figure 1:
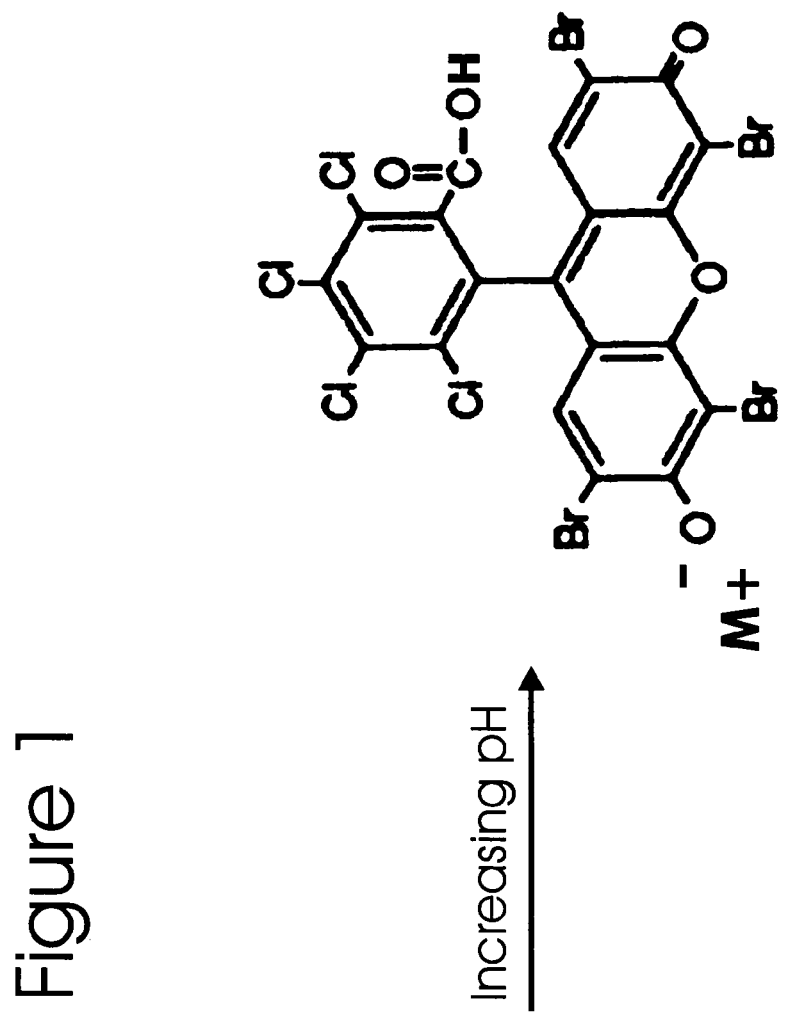
FIG. 1 shows the chemical structure of unbound Phloxine (colorless) and bound Phloxine (pink).
Figure 2:
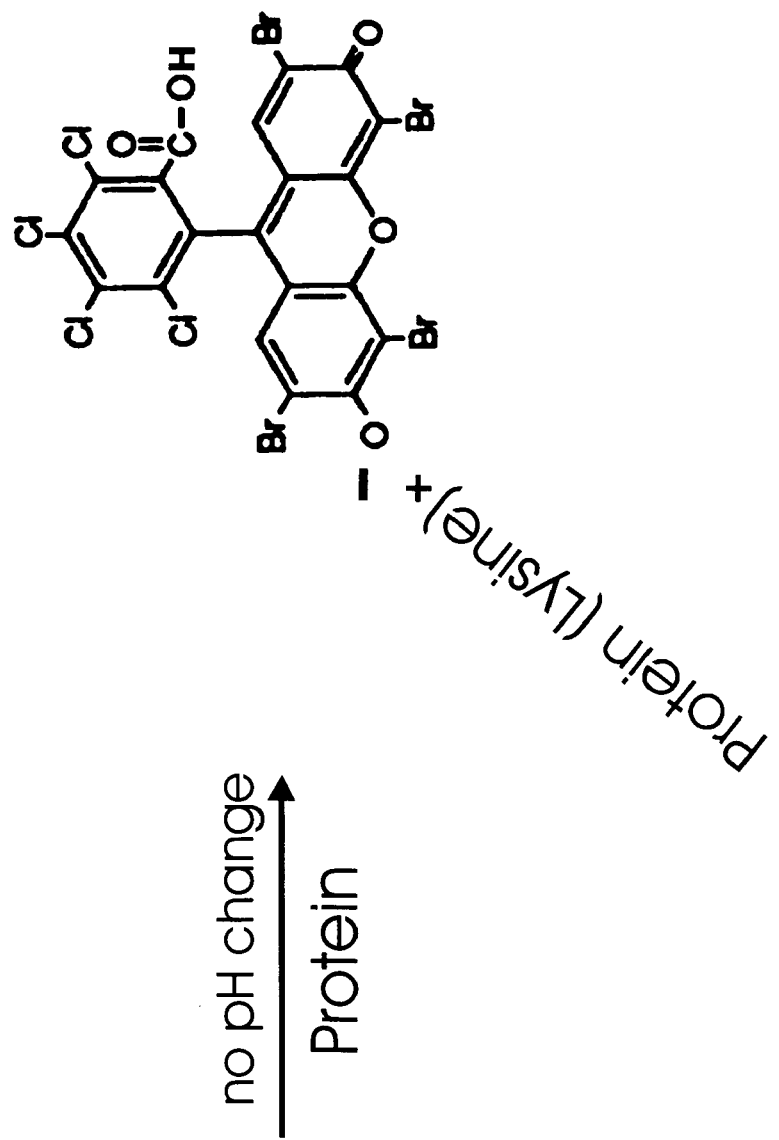
FIG. 2 shows a mechanism by which Phloxine attaches to protein.
Figure 2:
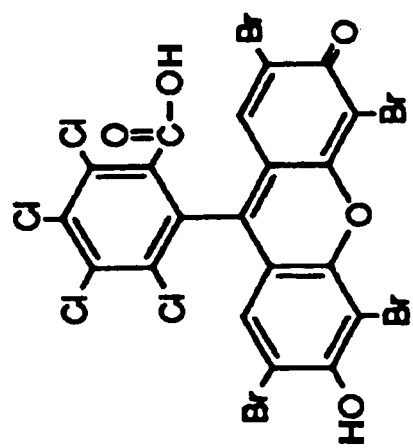

Disclosed herein is the use of Phloxine B, i.e., Acid Red 92 (CAS NO. 18472-87-2, $C_{20}H_2Br_4Cl_4Na_2O_5$. MOL WT. 829.64), hereinafter referred to as Phloxine, as a protein detector. Phloxine is a pH indicator that undergoes a visual color change based on it's pKa. Referring to FIG. 1, Phloxine goes from colorless (left) to red (right) between about pH 2-3.3, i.e., Phloxine is colorless below about pH 2, red above about pH 3.3 and varying shades of pink (pale to dark) between about pH 2-3.3. FIG. 2 shows a mechanism by which Phloxine attaches to protein thereby causing a color change from colorless (unbound) to red (bound) without a pH change. The pKa of unbound Phloxine occurs at about pH 2.8-2.9, if Phloxine is bound to a protein, the pKa shifts to the lower pH value of about 2-2.2. In a buffered system, this pKa shift changes the color of the indicator without a commensurate change in the pH. Unbound Phloxine will appear colorless at pH levels between about 2.3-3, whereas Phloxine bound to protein will appear pink at pH levels between about 2.3-3. Thus, buffering a sample at a pH below about 3 and contacting that sample with Phloxine enables the presence of protein to be detected in the sample via a color change from colorless to red. Optimally, the final combination of sample and Phloxine will result in a pH between about 2 and 2.5. Thus, depending on the conditions surrounding the Phloxine, the optimal buffering pH may vary, but should be below about 3.

Colorless to red as used herein means colorless to the entire spectrum of pink and red, including any and all shades of pink and red. Red shade color shifts are also possible if the starting color is something other than colorless. For example, if the starting color is blue, a red shade color shift to purple would be observed. Test strips containing Phloxine can be prepared by wetting a suitable paper substrate with a Phloxine solution and drying. Such test strips would be useful to those in the medical field.

Detection of Protein in Feline Urine

Disclosed herein is the incorporation of a health indicating system into an animal litter. Animal litters have been used for decades as an effective way of managing the sanitation and odor control of waste. Since animal health monitoring often involves the testing of waste materials from the animal, it would be desirable to combine a health monitoring system with an animal litter. Problems associated with developing such a system are unique in that the animal waste material has to be tested "as is", i.e., without the benefit of any sample preparation or "clean-up". For example, protein-indicating strips exist, but there are a number of limitations that prevent this technology from being used in an animal litter. Specific limitations with existing protein-indicating test strips include the following. (1) Stability of the indicator. Many protein-indicating compounds are not stable in the presence of elevated temperature, oxygen or moisture. (2) Stability of the color change. Many indicators do not hold the color change for long periods or when dry. Thus, a color change may occur without alerting the animal owner. (3) Color contrast. Many indicating systems rely on a subtle shift in the shade of a color, creating a system that is difficult for the user to interpret.

Accompanying the fact that the waste material must be used "as is", is the fact that feline urine, itself, is unique in several aspects. Feline urine contains high levels of salt. Thus, in inadequately buffered systems, the high salt content and the highly buffering nature of feline urine tends to overwhelm these systems creating numerous false positives. The gradual changes in color that result from inadequately buffered systems are difficult for the user to detect. Furthermore, the urine of healthy cats can contain some protein. Thus, the detection of protein in feline urine can only be an indicator of cat health if (1) normal levels of protein (500 ppm) can be distinguished from disease levels (2000 ppm) and (2) the color change can be easily interpreted. For applications of Phloxine as an indicator of feline health, color changes from colorless to pink rather than red are preferred by users. Thus, much of the discussion will revolve around systems exhibiting color changes from colorless to pink. However, it should be noted that, if desired, systems having color changes from colorless to red could readily be designed and substituted for those of colorless to pink.

Disclosed herein is a stable health indicating system which allows for the detection of protein in feline urine using an easily interpretable colorless to pink color change. Although the disclosure and examples focus on feline urine, as discussed previously, the system is applicable to mammalian urine in general. A protein sequestering agent, e.g., dodecyl (sulfophenoxy)benzenesulfonic acid (hereinafter DSB), is used to inhibit the color change at low levels of protein and allow the color change at higher levels. DSB competes strongly with the Phloxine for active sites on the protein and therefore, if present in a predetermined amount, the level of protein detection can be controlled. Referring to FIG. 3, DSB works by inhibiting the attachment of the Phloxine molecule to the active sites on the protein molecule thereby inhibiting a color change from occurring. Since the sequestering agent is present at a fixed level, it is effective in blocking attachment at low levels of protein, but at higher levels of protein free sites become available for the Phloxine to occupy, thus allowing the color change to occur. Compounds believed to denature proteins (as opposed to binding to them as DSB) could be used in place of the sequestering agent. Some examples of include Tritan™ surfactant, Nacconol™, and 5-sulfosalicylic acid.

Stock buffer solutions of citric acid which sometimes also contain sodium citrate (ranging from about 0.5-2.5M citric acid) can be used in preparing phloxine/DSB litter compositions as discussed in the Examples herein. Both Phloxine and DSB are very stable, i.e., no refrigeration is required and shelf life is not limited.

All or a portion of an absorbent litter material is coated or imbedded with the Phloxine/protein sequestering agent composition described. The Phloxine/protein sequestering agent composition can be added to the litter as a liquid spray, a powder coating or ingredient, a precoated particle, a speckle, or as part of an agglomerate litter. Suitable absorbent litter materials include minerals, fly ash, absorbing pelletized materials, perlite, silicas, other absorbent materials and mixtures thereof. Preferred minerals include: bentonites, zeolites, fullers earth, attapulgite, montmorillonite diatomaceous earth, opaline silica, Georgia White clay, sepiolite, calcite, dolomite, slate, pumice, tobermite, marls, attapulgite, kaolinite, halloysite, smectite, vermiculite, hectorite, Fuller's earth, fossilized plant materials, expanded perlites, gypsum and other similar minerals and mixtures thereof. The absorbent materials can be further processed, for instance by agglomeration. The lower the intrinsic pH of the substrate, the lower the amount of buffering agent needed. Thus, substrates having intrinsically low pHs relative to other substrates are preferred. When contacted with the animal urine, the Phloxine/protein sequestering agent composition changes to a color in the presence of high levels of protein and stays colorless in the absence of protein or in the presence of low levels of protein. Additional base colorants can be added to create a color change from one color to another color of a redder shade (e.g., blue to purple, etc.). Filler materials such as limestone, sand, calcite, dolomite, recycled waste materials, zeolites, and gypsum can also be incorporated with the absorbent materials to reduce the cost of the litter without significantly decreasing the material's performance as a health indicating litter.

Partial treatment of the litter can be accomplished by incorporating "treated speckles" into the base litter composition. Some problems associated with identifying effective speckle formulations include lack of color development, spontaneous color change, or bleeding of color. Effective speckle materials have the following properties: (1) Porous and rapidly absorbent; (2) Able to hold a high salt load; (3) Moderate surface area (about 25-300 $m^2/g$) and large pore size (greater than 400 Å); (4) Moderate surface acidity (pH between about 1-7) (5) Light color. Presumably, the high buffer loading and the rapid absorptivity allows for less influence from outside the particle. One material which fit the above-listed criteria is large pore size silica gel or Type MB macroporous silica gel. For example, a suspension of Phloxine B indicator, buffered at a pH of 2.1, with a trace of Rhodocal DSB-85, can be sprayed at a high loading rate (e.g., 20% or greater) onto Type MB Macroporous silica gel to form a "treated speckle". Incorporation of "treated speckles" into high pH clays such as bentonite can be accomplished, but care should be taken to avoid the Phloxine bleeding out of the speckle particles and turning red upon contact with the bentonite. For example, the litter can be layered to ensure that the Phloxine is bound up in an immobile layer, such as guar gum. Alternatively, a polymeric non-leaching indicator can be used in place of the Phloxine.

Non-litter applications of the combination of Phloxine/protein sequestering agent are also disclosed herein. For example, test strips containing Phloxine and DSB can be prepared and would be useful to those in the human or veterinarian medicine fields.

The following examples illustrate the present invention. The examples are for illustrative purposes only and are not meant to limit the scope of the invention in any way.

EXAMPLES

Materials

Bovine serum albumin (BSA) was obtained from either EMD Pharmaceuticals or Calbiochem was used as the protein detected in all examples listed below. BSA/water and BSA/urine standards were prepared. The urine used in BSA/urine standards was first treated by removing the native protein by precipitation with sulfosalicylic acid and filtration.

Phloxine was obtained from Aldrich Chemical. One percent phloxine solutions were prepared by dissolving phloxine in a small amount of methanol and then diluting with water.

The DBS used was Rhodacal DSB-85.

Stock buffer solutions of citric acid and sodium citrate can be used in preparing the phloxine/DSB litter compositions. For example, a buffer solution was prepared by adding citric acid to water and measuring the pH. Sodium citrate was then added to the citric acid solution, if necessary, until the pH reached the desired number.

Example 1

Preparation of Silica Gel Litter and Speckles

A Phloxine/Citric Acid/DSB solution comprising 0.1% Phloxine, 0.05% Rhodacal DSB-85, and the remainder 2M citric acid buffered with sodium citrate (adjusted to pH 2.15) was dripped on about 100 g of Macropore B silica gel until the absorption capacity of the silica gel was reached. The Phloxine/DSB-treated silica gel was then air-dried.

Example 2

Preparation of a Clumping Georgia White Clay (GWC) Litter

Sample 2A 4 g of a 1% phloxine solution and 0.077 g DSB were combined with 150 g of citric acid buffer (2M, pH 2). 35 g were applied to 50 g of GWC using a spray gun.

Sample 2B 2.7 g of the 1% phloxine solution were added to the solution prepared in Sample A to increase the phloxine concentration to 5%. 35 g of this solution were applied to 50 g GWC using a spray gun.

Sample 2C 2 g of the 1% phloxine solution were added to the solution prepared in Sample B to increase the phloxine concentration to 7.5%. 35 g of this solution were applied to 50 g GWC using a spray gun.

Sample 2D 1.125 g of the 1% phloxine solution were added to the solution prepared in Sample C to increase the phloxine concentration to 10%. 35 g of this solution were applied to 50 g GWC using a spray gun.

The GWC samples were allowed to dry for 2 days and then were tested with BSA/urine standards containing varying amounts of protein. The results are compiled in Table 1.

TABLE 1

|  | 700 ppm BSA/urine | 1200 ppm BSA/urine | 3200 ppm BSA/urine |
| --- | --- | --- | --- |
| Sample 2A | off-white | off-white | light pink |
| Sample 2B | off-white | light pink | Pink |
| Sample 2C | off-white | light pink | Pink |
| Sample 2D | off-white | light pink | Pink |

Example 3

Preparation of Silica Gel Litter with Health Indicating Speckels

Type C silica gel with about 5% health indicating speckels was prepared and tested. Macropore B silica gel was prepared as described in Example 1 and then added to a commercial Type C silica gel litter material.

Example 4

Preparation of Clay Litter with Health Indicating Speckels

A bentonite clay litter with about 3% health indicating speckels was prepared and tested. Macropore B silica gel was prepared as described in Example 1 and then added to a commercial bentonite litter material.

Example 5

Detection of Protein when Contacted with Sample Litter

The litter sample prepared in Example 3 was placed in a tray and tested with 2 ml of base urine (low protein) and 2 ml of 10K (theoretical), 3-5K (as analyzed) BSA/urine. The samples were evaluated after 4 hours and after 24 hours. The speckles contained in the section of sample tested with base urine remained white after 4 hours and remained unchanged after 24 hours. The speckles contained in the section of sample tested with a BSA/urine standard showed a pink hue after 4 hours and remained unchanged after 24 hours.

Another sample as described in Example 3 was prepared with a larger quantity of urine, about 5 ml, and allowed to stand for one week. The speckles contained in the section of sample tested with base urine remained white. The speckles contained in the section of sample tested with a BSA/urine standard contained regions of light pink and regions of bright pink. In all cases, the color was stable with little to no bleeding.

Example 6

Detection of Protein when Contacted with Sample Litter

The sample litter prepared in Example 4 was placed in a tray and tested with 5 ml of base urine (low protein) and 5 ml of 10 K (theoretical), 3-5K (as analyzed) BSA/urine. The samples after 4 hours and after 24 hours. The speckles contained in the section of sample tested with base urine showed regions of white and pink after 4 hours and remained unchanged after 24 hours. The speckles contained in the section of sample tested with a BSA/urine standard showed a few regions of white, some regions of light pink and some regions of darker pink after 4 hours and remained unchanged after 24 hours. Due to the high alkalinity of bentonite clay, some bleeding of color was expected to occur. Thus, the speckles were only partially successful in avoiding the influence of surrounding material.

Example 7

Preparation of Agglomerated Health Indicating Clay Liter 9.1 lbs of paste was prepared by mixing 7.8 lbs of guar gum and 1.3 lbs of citric acid, anhydrous and a small amount of water necessary to facilitate mixing. The paste was added to a mixture of: 69.9 lbs of Tennessee #10 Clay, 18.2 lbs of Kentucky Stone Clay, 2.7 lbs of citric acid (anhydrous), and 0.10 lbs Phloxine to form a litter mixture. Other similar clay materials could be substituted for the Tennessee #10 Clay and the Kentucky Stone Clay. The litter mixture was agglomerated through extrusion (or other agglomeration means) to form an agglomerated health indicating litter material.

It is to be understood that the invention described herein is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "buffering agent" includes two or more such agents.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

A number of methods and materials similar or equivalent to those described herein can be used in the practice of the present invention. Many modifications and variations are possible in light of the above teaching.

What is claimed is:

1. An animal litter additive comprising:
   MB Macroporous silica gel buffered at a pH below about 3 containing a mixture of a protein-sequestering agent and Phloxine, wherein said protein-sequestering agent is present in an amount effective at blocking the attachment of Phloxine to protein at a predetermined protein level.

2. The animal litter additive recited in claim 1, wherein said protein sequestering agent is dodecyl(sulfophenoxy)benzenesulfonic acid.

3. A protein detection method comprising:
   providing a sample;
   contacting said sample with Phloxine;
   contacting said sample with a predetermined level of a protein
   sequestering agent concurrent with the step of contacting said sample with Phloxine; and
   detecting the presence of protein in said sample, wherein a color change is observed if said sample contains said protein.

4. The method recited in claim 3, wherein the color change is a red shift.

5. The method recited in claim 3, wherein the Phloxine is buffered below a pH of about 3.

6. The method recited in claim 3, wherein said protein-sequestering agent is dodecyl(sulfophenoxy)benzenesulfonic acid (DSB).

7. The method recited in claim 3, wherein said contacting is accomplished by a test strip.

8. The method recited in claim 5, wherein said Phloxine is buffered using a weak acid and optionally a corresponding salt.

9. The method recited in claim 8, wherein said Phloxine is buffered using citric acid and optionally sodium citrate.

10. The method recited in claim 3, wherein the protein-sequestering agent is present in an amount effective at blocking the attachment of Phloxine to protein at a predetermined protein level.

11. The method recited in claim 10, wherein said predetermined protein level is between 500-2,000 ppm.

12. The method recited in claim 10, wherein said predetermined protein level is greater than 2,000 ppm.

13. The method recited in claim 3, wherein said sample is a urine sample.

14. The method recited in claim 13, wherein said urine is mammalian urine.

15. The method recited in claim 14, wherein said mammalian urine is human, canine, feline, equine, bovine, lupine or rodent.

16. An animal litter comprising:
   An absorbent material suitable for use as an animal litter, wherein at least a portion of said litter contains Phloxine, wherein said Phloxine-containing portion of litter is below about pH 3; and
   contains a predetermined amount of a protein-sequestering agent wherein the predetermined amount of protein-sequestering agent is the amount effective at blocking the attachment of Phioxine to protein at a predetermined level.

17. The animal litter recited in claim 16, wherein said absorbent material is selected from the group consisting of bentonites, zeolites, fullers earth, attapulgite, montmorillonite diatomaceous earth, opaline silica, Georgia White clay, sepiolite, calcite, dolomite, slate, pumice, tobermite, marls, attapulgite, kaolinite, halloysite, smectite, vermiculite, hectorite, Fuller's earth, fossilized plant materials, expanded perlites, gypsum and mixtures thereof.

18. The animal litter recited in claim 17, wherein the protein-sequestering agent is dodecyl(sulfophenoxy)benzenesulfonic acid (DSB).

* * * * *